United States Patent [19]

Heggeness et al.

[11] Patent Number: 5,514,180
[45] Date of Patent: May 7, 1996

[54] PROSTHETIC INTERVERTEBRAL DEVICES

[76] Inventors: Michael H. Heggeness, 3301 Drummond, Houston, Tex. 77025; Brian J. Doherty, 350 Sharon Park Dr. Apt. E 39, Menlo Park, Calif. 94025

[21] Appl. No.: 182,294

[22] Filed: Jan. 14, 1994

[51] Int. Cl.⁶ .................................................. A61F 2/44
[52] U.S. Cl. .............................. 623/17; 606/60; 606/61
[58] Field of Search .............................. 623/16, 17, 18; 606/60, 61, 62, 69, 72

[56] References Cited

U.S. PATENT DOCUMENTS

| | | |
|---|---|---|
| 5,108,438 | 4/1992 | Stone . |
| 5,123,926 | 6/1992 | Pisharodi ........................... 623/17 |
| 5,147,404 | 9/1992 | Downey ............................. 623/17 |
| 5,171,278 | 12/1992 | Pisharodi ........................... 623/17 |
| 5,171,280 | 12/1992 | Baumgartner ....................... 623/17 |
| 5,171,281 | 12/1992 | Parsons et al. ..................... 623/17 |
| 5,192,327 | 3/1993 | Brantigan .......................... 623/17 |
| 5,314,478 | 5/1994 | Oka et al. ....................... 623/17 X |

FOREIGN PATENT DOCUMENTS

| | | | |
|---|---|---|---|
| 4220218 | 12/1993 | Germany ........................... 623/17 |
| 8707827 | 12/1987 | WIPO .............................. 623/17 |
| 9423671 | 10/1994 | WIPO .............................. 623/17 |

OTHER PUBLICATIONS

Brantigan, J. W. and Steffee, A. D., "A Carbon Fiber Implant to Aid Interbody Lumbar Fusion," *Spine*, 18:2106–2117 (1993).
Bagby, G. W., "Arthrodesis by the Distraction–Compression Method Using a Stainless Steel Implant," *Orthopedics*, 11:931–934 (1988).
Kaneda, K., et al., "The Treatment of Osteoporotic–Post-–traumatic Verterbral Collapse Using the Kaneda Device and a Bioactive Ceramic Vertebral Prosthesis," *Spine*, 17:S295–303 (1992).
AcroMed Product Bulletin—AcroFlex Artificial Disc (1993).
AMS Product Bulletin—Amset RSF Rezaian Spinal Fixator (1991).
Cook, S. D., et al., "In Vivo Evaluation of Recombinant Human Osteogenic Protein (rhOP–1) as a Bone Graft Substitute for Spine Fusions," Paper #16 General Session Abstracts from 8th Annual NASS Meeting, Oct. 14–16, 1993 (San Diego, CA).
Baylink, D. J., et al., "Growth Factors to Stimulate Bone Formation," J. Bone and Mineral Research. 8:S565–572 (Dec. 1993).
White, A. A. and Panijabi, M. M., *Clinical Biomechanics of the Spine*, 2nd Ed., pp. 596–598 (1990).

Primary Examiner—Mary B. Jones
Attorney, Agent, or Firm—Laura G. Barrow

[57] ABSTRACT

Disclosed are prosthetic devices for insertion into intervertebral disc spaces after the removal of an intervertebral disc or after a corpectomy. Specifically, intervertebral devices having fixed shapes for accommodating the defined surface contours of vertebral endplates are disclosed. Also disclosed are intervertebral devices formed of osteoinductive materials, such as bone growth factors, to facilitate bone growth. A method for quantitatively determining the three-dimensional morphology of vertebral surfaces, particularly vertebral endplates, is also disclosed.

36 Claims, 15 Drawing Sheets

PROSTHETIC INTERVERTEBRAL DEVICES

BACKGROUND OF INVENTION

1. Field of Invention

The present invention is directed to anterior prosthetic intervertebral devices which may be inserted in the vertebral disc spaces resulting from the removal of diseased or damaged intervertebral discs. The present invention is also related to prosthetic intervertebral devices for insertion in the space resulting between non-contiguous vertebrae following a corpectomy. In particular, the present inventive intervertebral devices have specific, fixed shapes designed to accommodate the normal morphological anatomy of anterior vertebral endplates, particularly in the thoracic and lumbar regions of the spine, for better stability and fit. The present invention is further related to a method of determining the specific morphology of the surfaces of vertebral bodies, more particularly anterior vertebral endplates.

2. Description of the Related Art

Devices for Intervertebral Disc Space Repair:

In surgery, there are frequently indications for total or near total removal of an intervertebral disc from an anterior approach. On some occasions, a corpectomy is required wherein the entire vertebral body itself is removed because of fracture, tumor, or deformity. The subsequent space created by these procedures which corresponds to the space vacated by the disc (or by two discs and the intervening vertebral body resulting after a corpectomy) needs to be reconstructed in surgery.

One of the most well-established methods of intervertebral space reconstruction involves the careful placement of an autograft (i.e. bone graft) between the two vertebral endplates (i.e. the superior endplate of one vertebra and the inferior endplate of a second vertebra). The autograft will bear weight across the surgical defect and ultimately initiate bony union or healing between the graft and the adjacent vertebrae. These autografts, which can be obtained from the fibula or the pelvis, are excised from the patient undergoing surgery and then shaped by the surgeon to fit the proper intervertebral space.

Another method of intervertebral space reconstruction is the use of allografts. Allografts are bones obtained from another human individual (most are usually harvested from voluntary donors after death). These allografts can be prepared in numerous ways, with the process including aggressive washing and radiation sterilization, and can be produced in a variety of sizes and shapes. Allograft sections of human femur are a popular choice and can be purchased with flat upper and lower surfaces in various heights. These allograft femur segments are shaped and sometimes shortened by the surgeon at the time of surgery, and then placed into the spaces created by the surgical removal of a disc or vertebral body. As with the autografts, these allografts are intended to heal the adjacent vertebral endplates together.

There are also available intervertebral devices designed to augment the weight bearing capacity of the applied graft as well as allow the use of morselized or fragmented non-structural grafts. These devices include shaped titanium cages and graphite (carbon fiber) boxes, both of which are manufactured in a variety of sizes and lengths. The titanium cage is manufactured with a flat top and bottom. The graphite box is also currently manufactured with parallel flat surfaces on the top and bottom. Both devices are intended to bear weight across a corpectomy interval or intervertebral disc space interval and allow the packing of cancellous autografts or allografts into the space.

A more elaborate device intended to accomplish a similar purpose as the titanium cage and graphite box is the AMSET Rezaian Spinal Fixator. This mechanical device is designed to be placed into defects to allow a mechanical distractive force to be applied through the created defect. This device also has a flat surface on top and bottom which is augmented by conical teeth which engage the superior and inferior vertebral endplates.

Another device is Spine-Tech, Inc.'s BAK Spinal Stabilization System. This device is a threaded cylinder intended to be placed across a disc space to obtain screw fixation in the superior endplate of one vertebra and the inferior endplate of a second vertebra.

Kaneda, K., et al. (*Spine*, 17: S295–S303 (1992) report the use of ceramic vertebral prostheses, more specifically the use of these ceramic implants along with the Kaneda device for the treatment of osteoporotic posttraumatic vertebral collapse. These implants are generally rectangular in shape and have substantially flat upper and lower surfaces. The researchers report on page S296 that the vertebral body surfaces should be shaved to touch firmly the ceramic implant.

A very different approach to intervertebral space reconstruction is total disc replacement. One total disc replacement design is the Steffee design manufactured by AcroMed. This device consists of a deformable plastic insert attached to a flat metal surface above and below. These flat metal surfaces have conical teeth, similar to those of the Rezaian Spinal Fixator, that are intended to engage the vertebral endplate. Another deformable plastic disc analog is that designed by Dr. Casey Lee of New Jersey Medical School which is contoured with arbitrarily selected curved surfaces above and below the implant.

Another intervertebral disc utilizes the Kostuik disc design. This disc also has a flat upper and lower endplate; however, instead of a deformable plastic disc analog, this implant uses metal mechanical springs.

U.S. Pat. No. 5,171,278 to Pisharodi is directed to an expandable artificial disc prosthesis. More specifically, it is directed to cylindrical and rectangular disc implants which are expandable in the middle to contact the vertebral bodies.

None of the foregoing devices are designed to accommodate the defined anatomical contours of the vertebral endplate. Consequently, these devices contact only a minimal number of points on the surfaces of the vertebral endplates. Such an uneven distribution of stress exerted by the adjacent vertebrae upon the devices further results in an increase risk of subsidence and collapse of the device.

U.S. Pat. No. 5,123,926 to Pisharodi is directed to a spring-loaded, middle expandable total disc prosthesis. The disc is comprised of an elastic bag having a plurality of spikes which extend upward from the superior surface, and downward from the inferior surface of the disc. The disc may be expanded to fill the disc space by injecting a liquid or gas substance into the disc. Such expansion of the disc results in an increase number of contact points between the disc and the surface of the vertebral endplates. However, the elastic disc is much more susceptible to wear and ultimately collapsing once implanted in the human body due in part to the nature of the elastic material (rubber, silicone rubber, and plastic, for example) required for disc expansion. Moreover, the design of the disc precludes the incorporation of osteoinductive materials, such as bone growth factors, for example, which assist in bone fusion.

The goal in practically every case of intervertebral disc space reconstruction is to achieve bony fusion between the vertebral endplates and the intervertebral device. Unfortunately, bone grafts do not always heal reliably, with some studies reporting failure rates (i.e. failure of adequate bone fusion) ranging from 10% to as high as 40%. Without complete bone fusion of the vertebral endplates with the intervertebral device or graft, the vertebrae adjacent to device or graft is less stable, often necessitating further surgery. Consequently, attempts have been made to facilitate bone growth. One technique is to apply electrical stimulation to the graft, as accomplished by several devices manufactured by the E.B.I. Company. The application of electrical stimulation to the bone is theorized to promote bone growth into the device.

It is therefore desirable to have an intervertebral device for use in intervertebral disc space reconstruction resulting from the removal of a single disc, or a total corpectomy, that:

1) has defined contours or shapes that are designed to accommodate the normal and predictable morphological anatomy of the vertebral endplates, resulting in significantly better stress distribution along the endplate;

2) is formed of a durable and physiological compatible material that will better endure the forces exerted upon it by the adjacent vertebral bodies; and/or 3) is formed of, or designed to, accommodate an osteoinductive material such as bone growth factors to facilitate bone fusion into the intervertebral device faster and more reliably for better repair of the disc space.

Morphology of vertebral bodies:

The increase in popularity of lumbar interbody fusion and the design of many interbody implants has created the need for a more quantitative anatomical description of the vertebral column. In particular, recent investigations of vertebral mechanics have shown that the vertebral endplate plays an important role in supporting stresses passed through the intervertebral disc. This leads to the suggestion that endplate resection during surgery may compromise the ultimate strength and/or stability of the surgical construct.

The literature contains many studies of the anatomy of the spinal column. J. L. Berry, et al ["A Morphometric Study of Human Lumbar and Selected Thoracic Vertebrae," Spine, 12:362–367 (1987)] measured twenty-seven dimensions in the thoracic and lumbar vertebrae using dried spinal columns from thirty skeletons. In addition to overall dimensions, they record the angle between inferior and superior endplates. M. Nissan and I. Gilad ["The Cervical and Lumbar Vertebrae—An Anthropometric Model," Eng. Med., 13(3):111–114 (1984)] performed a study of vertebral dimensions which also described the overall angle between endplates on each vertebra. P. V. Scoles, et al. ["Vertebral Body and Posterior Element Morphology—The Normal Spine in Middle Life," Spine, 13:1082–1086 (1988)] conducted a study on vertebral body morphology which was focused primarily on the posterior elements.

M. M. Panjabi et al ["Thoracic Human Vertebrae—Quantitative Three-Dimensional Anatomy," Spine: 16:888–901 (1991)] conducted an extensive study on the three-dimensional disc anatomy of thoracic and lumbar vertebrae. These researchers devised their measurements into linear parameters, surface and cross-sectional area parameters, and angular parameters. Measurements of the vertebral body were limited to endplate width, endplate area, and endplate inclination (i.e. the angle between the best-fit planes for each endplate).

For purposes of developing intervertebral implants designed to better fit the specific contours of the surfaces of adjacent vertebral bodies, particularly vertebral endplates in the thoracic and lumbar spinal regions, it is desirable to have a method for quantitatively determining the three-dimensional morphology of these vertebral surfaces. Such a method would be useful in designing a series of intervertebral devices and implants having defined surface shapes which compliment or accommodate the defined morphology of the adjacent vertebral surfaces. Additionally, such a method could be used to measure individual vertebral surfaces of an individual patient for purposes of customizing an intervertebral endplate to accommodate the patient's individual anatomy.

SUMMARY OF THE INVENTION

The present invention, in certain embodiments, is directed to prosthetic intervertebral devices designed to accommodate the specific morphological anatomy of vertebral endplates, in particular vertebral endplates located in the thoracic and lumbar region of the spine. Based on a detailed quantitative study of the morphology of the vertebral endplates in this region of the spine (primarily thoracic-11 (T-11) through lumbar-5 (L-5)), five morphological types of surfaces were defined: three types of superior vertebral endplate surfaces and two types of inferior vertebral endplate surfaces. The present inventive implants thus comprise specific contoured inferior and superior surfaces which are capable of accommodating the defined morphological anatomy of a given superior and inferior vertebral endplate, respectively. Once inserted into the intervertebral disc space, the inventive devices aid in reconstruction of the disc space resulting from the removal of a single damaged or diseased disc or from a complete corpectomy (i.e. the removal of two discs and an intervening vertebral body), for example.

The present invention is also directed to intervertebral devices formed of, or designed to incorporate, various osteoinductive materials such as bone growth factors, for example. Such materials serve to facilitate bone growth into the device for better stabilization and improved reconstruction of the disc space following the removal of a single damaged or diseased disc or from a complete corpectomy, for example.

Finally, the present invention relates to a quantitative method of determining the three-dimensional morphology of the surfaces of vertebral bodies, particularly vertebral endplates. The inventive method allows for the development of prosthetic intervertebral devices having defined contours on their surfaces that are designed to accommodate the specific morphology of the vertebral surfaces with which the device comes in contact.

BRIEF DESCRIPTION OF THE DRAWINGS

The objects, advantages, and features of the invention will become more apparent by reference to the drawings which are appended hereto, wherein like numerals indicate like parts and wherein an illustrated embodiment of the invention is shown, in which.

DETAILED DESCRIPTION OF THE PREFERRED EMBODIMENT

Figure 1:
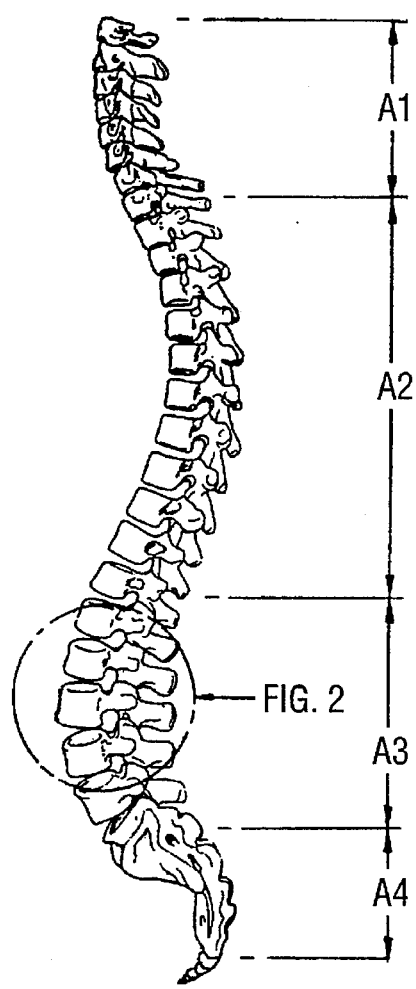
FIG. 1 is a left side elevation view of the spinal column (A) showing the cervical spinal region (A1), the thoracic spinal region (A2), the lumbar spinal region (A3), and the sacral spinal region (A4).
Figure 2:
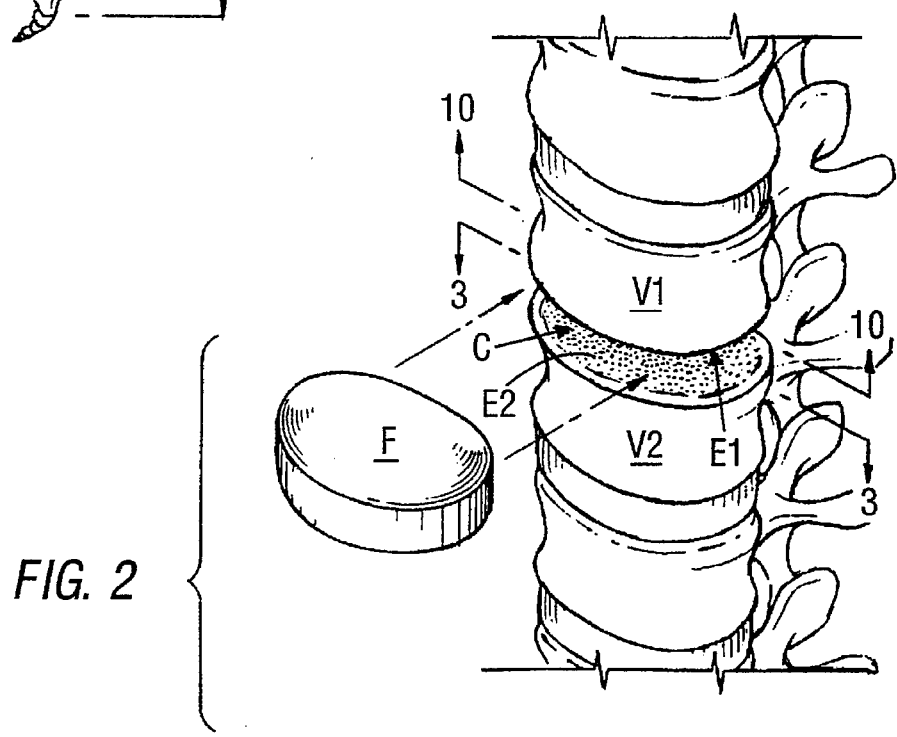
FIG. 2 is a detailed perspective view of FIG. 1 showing the front and left sides of lumbar vertebrae as well as one embodiment of the inventive intervertebral device.

The present invention is related to prosthetic intervertebral devices intended to replace an intervertebral disc which has been removed due to disease, infection, deformity, or fracture, for example. In certain embodiments, the present invention further comprises intervertebral devices for insertion into an intervertebral space resulting from a corpectomy for repair thereof. As shown in FIG. 2, the inventive device (F) is inserted into the resulting disc space (C) located between the superior endplate (E2) of the inferior vertebra (V2) and the inferior endplate (E1) of the superior vertebra (V1) (each vertebral body has a superior endplate and an inferior endplate). In the present invention, certain embodiments of the inventive devices are designed to accommodate the defined contours (i.e. shapes) of superior and inferior endplates of vertebral bodies, particularly those in the thoracic and lumbar spinal region, as shown, for example, in FIGS. 1 and 2. Specifically, certain embodiments of the present invention comprise:

(a) a body for insertion into an intervertebral disc space;

(b) a superior surface integral with the body and having a fixed shape to accommodate defined contours of an inferior vertebral endplate; and (c) an inferior surface integral with the body and having a fixed shape to accommodate defined contours of a superior vertebral endplate.

Based on an extensive quantitative anatomical study of the morphology of vertebral endplate surfaces in the thoracic and lumbar spinal regions (primarily T-11 through L-5), as discussed further in Examples 1–3, the defined contours or shapes of these vertebral endplates may be categorized into five groups: "ramp," "saddle," "irregular," "bowl," and "hump." The ramp, saddle, and irregular contours are primarily found on the superior endplates of the thoracic and lumbar spinal region, while the inferior endplates of this spinal region are primarily either hump-shaped or bowl-shaped. Certain embodiments of the present invention thus comprise rigid fixed shapes on their inferior and superior surfaces to accommodate these defined contours of the endplates. Thus, for example, a disc space defined by a saddle-shaped superior endplate of an inferior vertebral body and a bowl-shaped inferior endplate of a superior vertebral body would necessitate an embodiment of the inventive device having a superior surface and an inferior surface contoured or shaped to accommodate the "bowl" and "saddle" contours of the endplates, respectively.

By incorporating such fixed shapes to the inventive intervertebral devices, the stresses and forces exerted on the device by the spine are significantly better distributed along the surfaces of the device due to the increase number of contact points between the surface of the inventive device and the respective vertebral endplates. As a result, the disc space is more stable during the repair, and the inventive device will be less likely damaged or deformed over time. This latter aspect of the present inventive devices, i.e. a greater resistance to wear and tear in the body, is particularly advantageous since these devices are intended to remain in the patient permanently in the majority of cases.

Since the dimensions of the contours of the vertebral endplates may vary from patient to patient, the size of the specific fixed shapes of the inventive devices (in terms of depth, height, lateral width, and anterior/posterior length, for example) will vary. Consequently, all of the preferred size and dimension ranges discussed herein for the specific fixed shapes of the inventive devices are based upon an extensive quantitative study on sixty-seven vertebrae, discussed further in Examples 1–3. In practice, however, variations outside of these ranges may be necessary depending upon the anatomy of the individual patient.

Moreover, while certain embodiments of the present invention are designed primarily for use in the thoracic and lumbar region (especially T-11 through L-5), the inventive devices may be further modified to accommodate the defined contours of vertebral surfaces in the cervical and upper thoracic spine, preferably vertebral endplates of the cervical and thoracic-10 spinal region.

Figure 3:
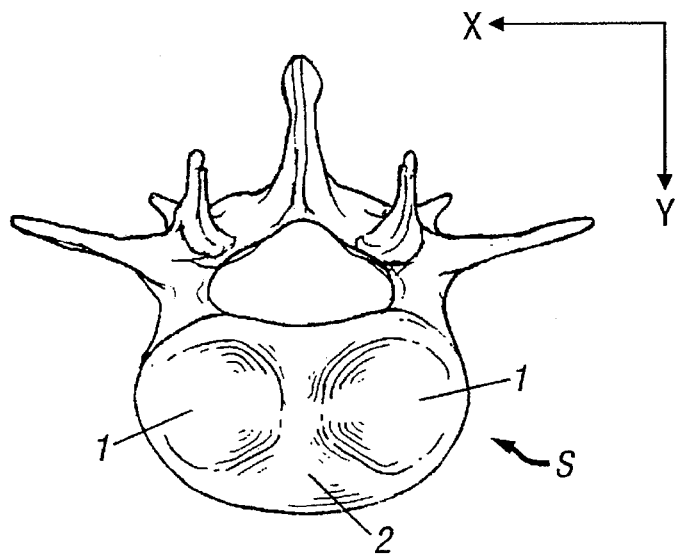
FIG. 3 is a top view taken along line 3—3 of FIG. 2 showing a superior vertebral endplate having a "saddle" shape.
Figure 3A:
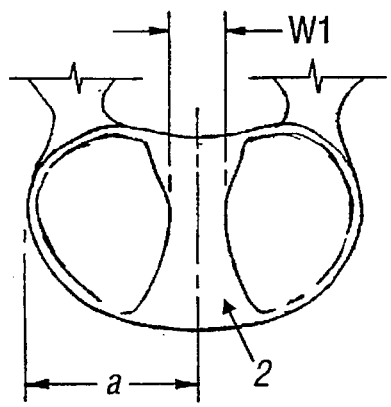
FIG. 3A is a schematic top view of the saddle contour of a superior vertebral endplate.
Figure 4:
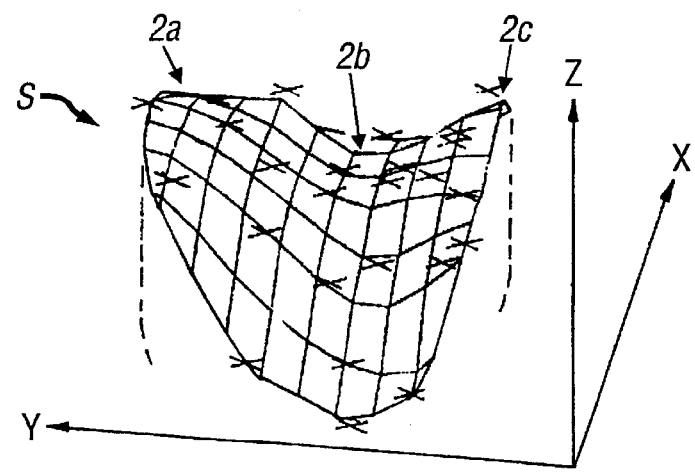
FIG. 4 is a 3-dimensional computer-generated plot of a "saddle-shaped" superior vertebral endplate, the vertical scale of which has been expanded 10×.
Figure 5:
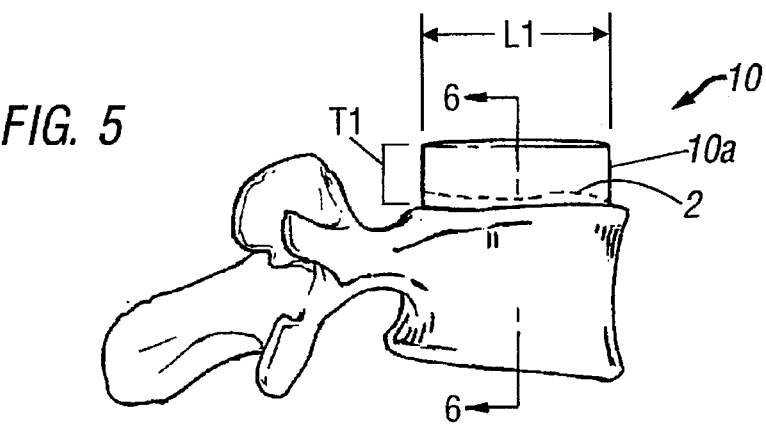
FIG. 5 is a side elevation view of the inventive device positioned on the surface of the "saddle-shaped" superior vertebral endplate.
Figure 6:
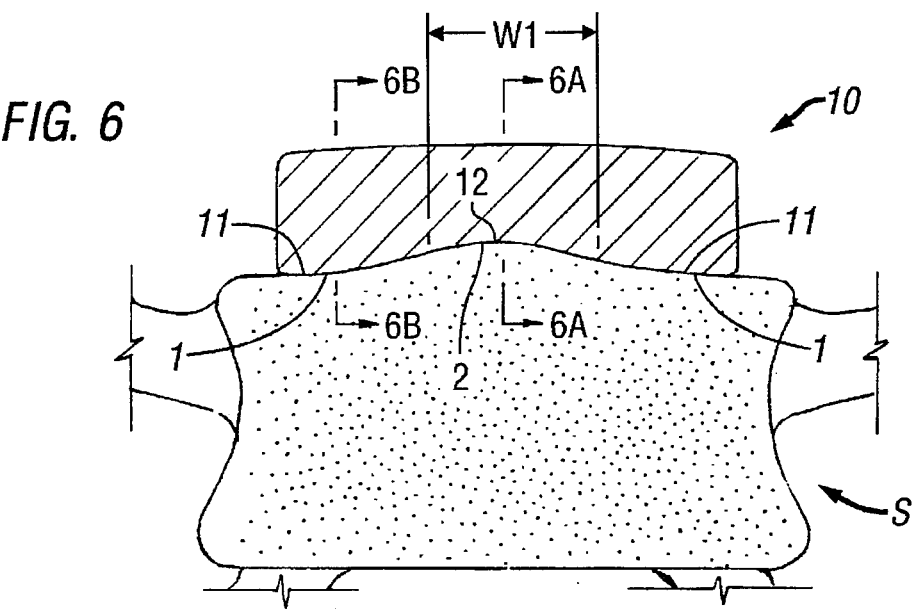
FIG. 6 is a front elevation view taken along lines 5—5 of FIG. 5.
Figure 6A:
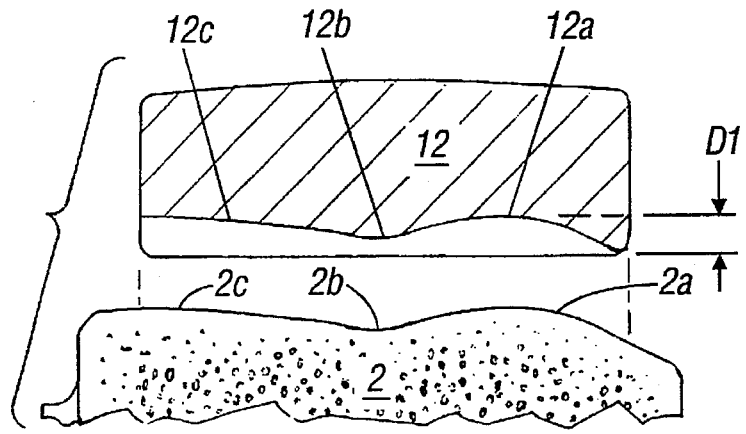
FIG. 6A is an exploded cross-sectional view of the endplate and device taken along lines 6a—6a of FIG. 6.
Figure 6B:
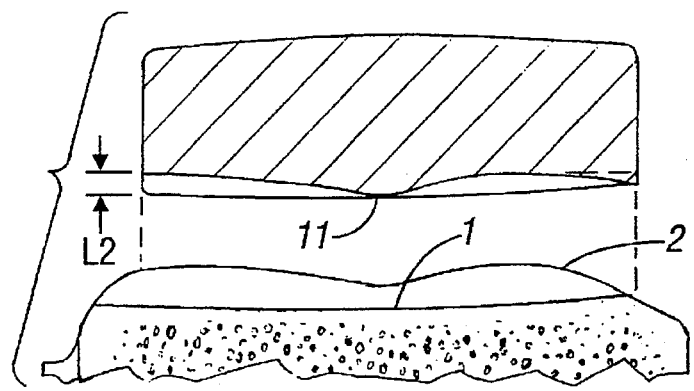
FIG. 6B is an exploded cross-sectinal view of the endplate and device taken along lines 6b—6b of FIG. 6.
Figure 7:
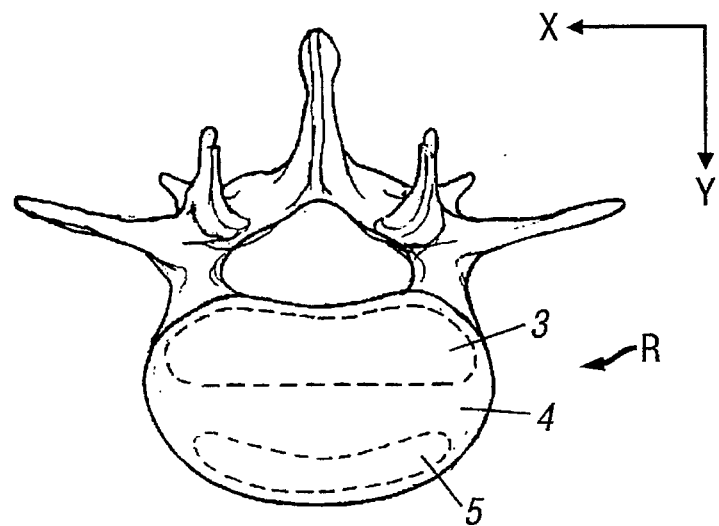
FIG. 7 is a top view of a superior vertebral endplate having a "ramp" shape.
Figure 8:
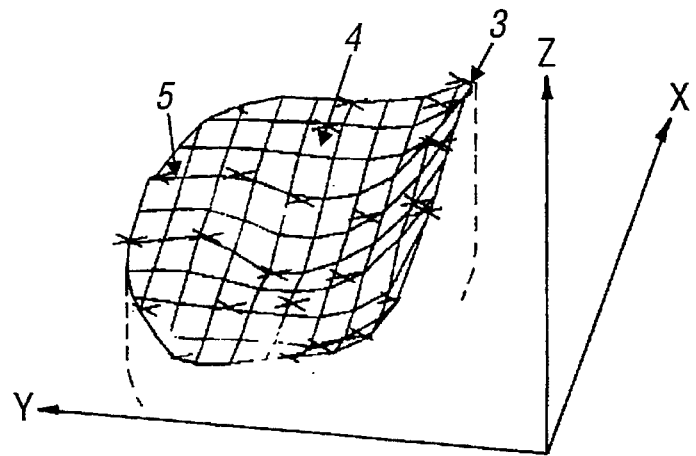
FIG. 8 is a 3-dimensional computer-generated plot of a "ramp-shaped" superior vertebral endplate, the vertical scale of which has been expanded 10×.

FIGS. 2–6 illustrate the "saddle" contour of a superior endplate (S) in the lower thoracic and lumbar spinal regions. This contour, which covers substantially the entire endplate surface, comprises two concavities (1) positioned side by side in the lateral dimension of the endplate, and an elevated ridge (2) positioned centrally between the two concavities. [The phrase "lateral dimension," as used herein, refers to the left end to right end dimensions of the endplate or inventive device along the X-axis. Similarly, the phrase "anterior/posterior dimension," as used herein, refers to the surface extending from the anterior end to the posterior end of the endplate or inventive device along the Y-axis.]. This elevated ridge (2) is typically convex in shape when viewed from the front, as shown in FIG. 6, and positioned approximately in the center (a) of the endplate surface (i.e. about 50% of the lateral dimension), as shown in FIG. 3A. The elevated ridge (2) generally includes, in a series, a convexity (2a) positioned anteriorly on the ridge, a central concavity (2b) adjacent to the convexity (2a) and positioned centrally along the anterior/posterior dimension, and a posterior ramp (2c) positioned posteriorly on the ridge and adjacent to the central concavity (2b). This ramp (2c) typically extends upward toward the posterior side of the endplate. The lateral width (W1) of the elevated ridge is generally from about 5 mm to about 15 mm.

FIGS. 5, 6, 6A, and 6B also illustrate an embodiment of the present invention (10) designed to accommodate a superior endplate having a saddle-shaped surface. In particular, the fixed shape of the inferior surface integral with the body (10a) of this embodiment comprises two convexities (11) positioned bilaterally to one another along the lateral dimension of the device to accommodate the two concavities (1) of the endplate surface. The fixed shape of the inventive device further includes a longitudinal portion (12) positioned centrally between the two convexities (11) and extending along the anterior/posterior dimension. The longitudinal portion (12) preferably comprises, in a series, a concavity (12a) positioned anteriorly on the device to accommodate the convexity (2a) of the elevated ridge (2), a centrally positioned convexity (12b) adjacent to the concavity (12a) for accommodating the central endplate concavity (2b), and a posterior ramp (12c) adjacent to the centrally positioned convexity (12b) to accommodate the remaining contours of the elevated ridge (i.e. the posterior endplate ramp (2c)).

As shown in FIGS. 5, 6, 6A, and 6B, the two lateral convexities (11) of the inferior surface of the device are intended to rest securely within (i.e. accommodate) the respective concavities (1) of the superior endplate. Likewise, the longitudinal portion (12) is intended to rest onto (i.e. accommodate) the elevated ridge (2) of the endplate. Thus, the height of each lateral convexity (11) in the inventive embodiments depicted in FIGS. 5, 6, 6A, and 6B is preferably the same as the depth of each of the concavities of the superior endplate, specifically from about 2 mm to about 5 mm (L1). Further, the depth (D1) of the longitudinal portion (12) preferably approximates the height of the elevated ridge, i.e. from about 1 mm to about 4 mm. In addition, the lateral width of the longitudinal portion is the same as that of the elevated ridge (W1), preferably from about 5 mm to about 15 mm.

FIGS. 7–10 illustrate the "ramp" contour of a superior endplate (R) in the lower thoracic and lumbar spinal regions. This contour, which covers substantially the entire endplate surface, comprises, in a series from the posterior end to the anterior end of the endplate (i.e. along the Y-axis), a declining ramp (3), and a substantially flat plane (4) extending from the declining ramp and further extending slightly upward into a substantially rounded ridge (5) positioned anteriorly along the endplate surface.

Figure 9:
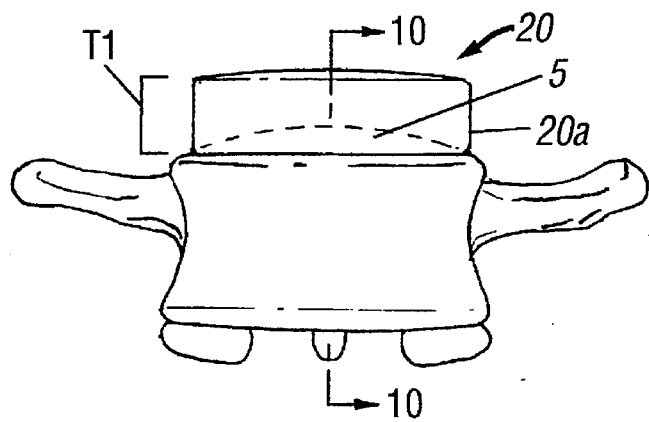
FIG. 9 is a front elevation view illustrating another embodiment of the inventive device positioned on the surface of the "ramp-shaped" superior vertebral endplate.
Figure 10:
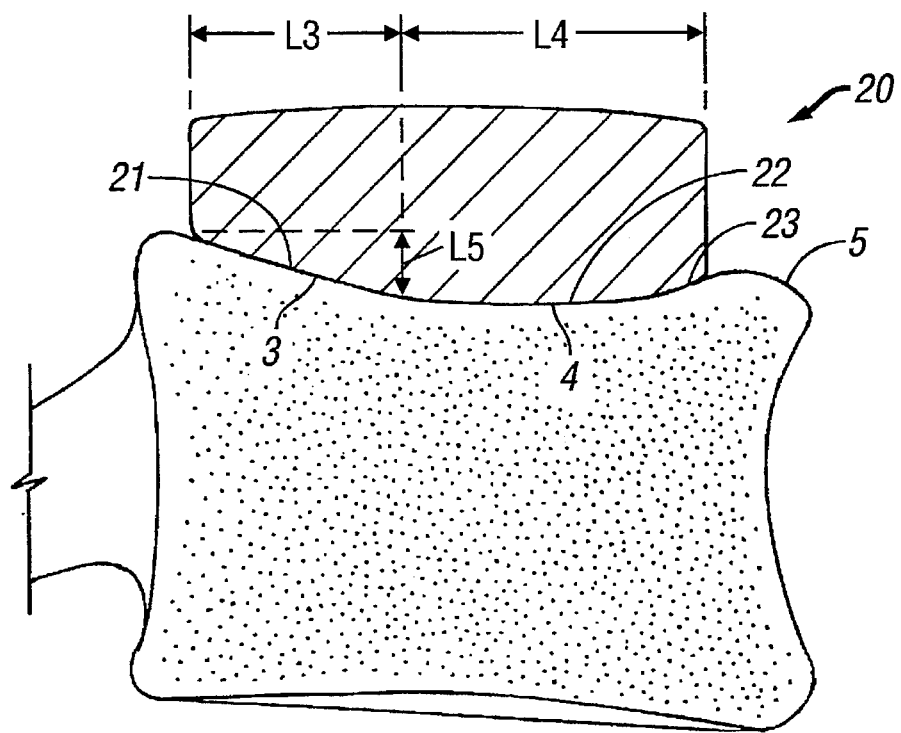
FIG. 10 is a side sectional view taken along lines 10—10 of FIG. 9.

FIGS. 9 and 10 illustrate an embodiment (20) of the present invention designed to accommodate a superior endplate having a ramp-shaped surface integral with its body (20a). In particular, the fixed shape of this embodiment includes, in a series, a ramp (21) positioned posteriorly on the surface and designed to accommodate the declining ramp (3) of the endplate, and a substantially flat lower plane (22) extending from the ramp (21) for accommodating the plane (4) of the endplate, and which preferably inclines slightly upward into a rounded end (23). Thus, the dimensions of the elements of the fixed shape of this embodiment preferably approximate the dimensions of the contours of the ramp shaped endplate. Preferably, the length (L3) of the ramp (21) is from about 10 mm to about 30 mm, and the length (L4) of the lower plane (22) is preferably from about 10 mm to about 40 mm. In addition, the ramp (21) is positioned at an angle sufficient to accommodate the depth (L5) of the ramped contour, which is generally from about 2 mm to about 4 mm.

Figure 11:
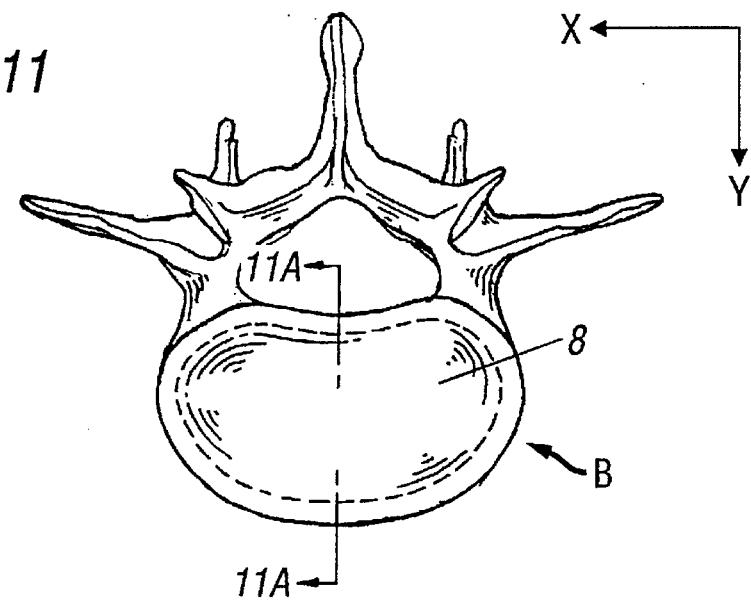
FIG. 11 is a bottom view taken along line 11—11 of FIG. 2 showing an inferior vertebral endplate having a "bowl" shape.
Figure 11A:
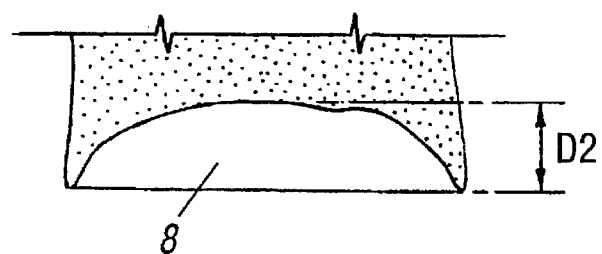
FIG. 11A is a schematic side view of a bowl contour of an inferior vertebral endplate.
Figure 12:
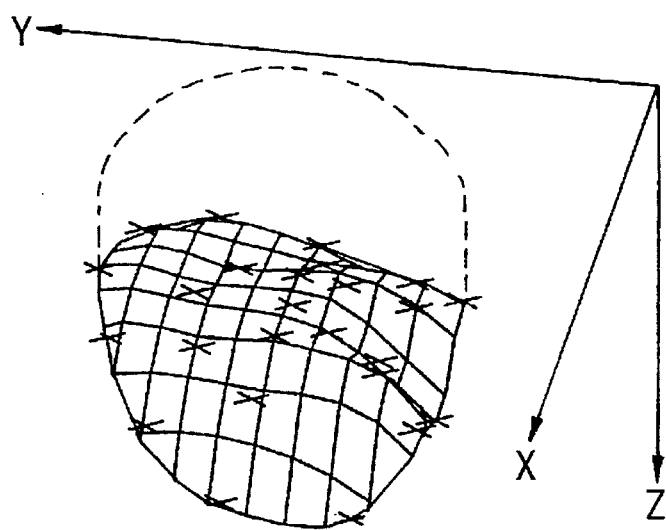
FIG. 12 is a 3-dimensional computer-generated plot of a "bowl-shaped" inferior vertebral endplate, the vertical scale of which has been expanded 10×.
Figure 13:
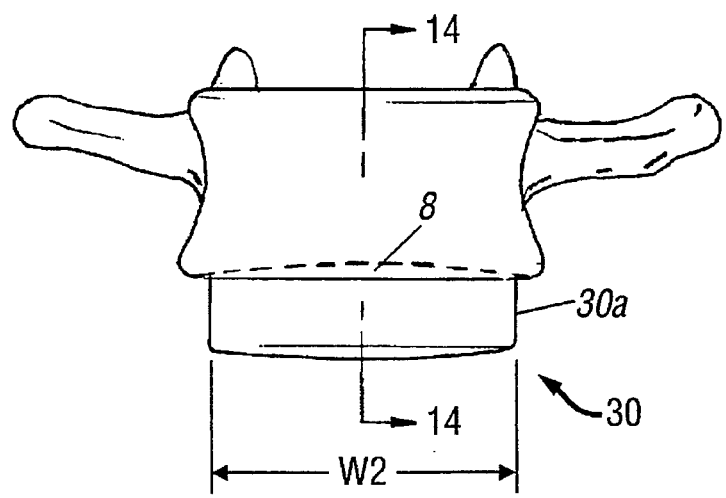
FIG. 13 is a front elevation view of one embodiment of the inventive device positioned on the bowl shaped inferior vertebral endplate.
Figure 14:
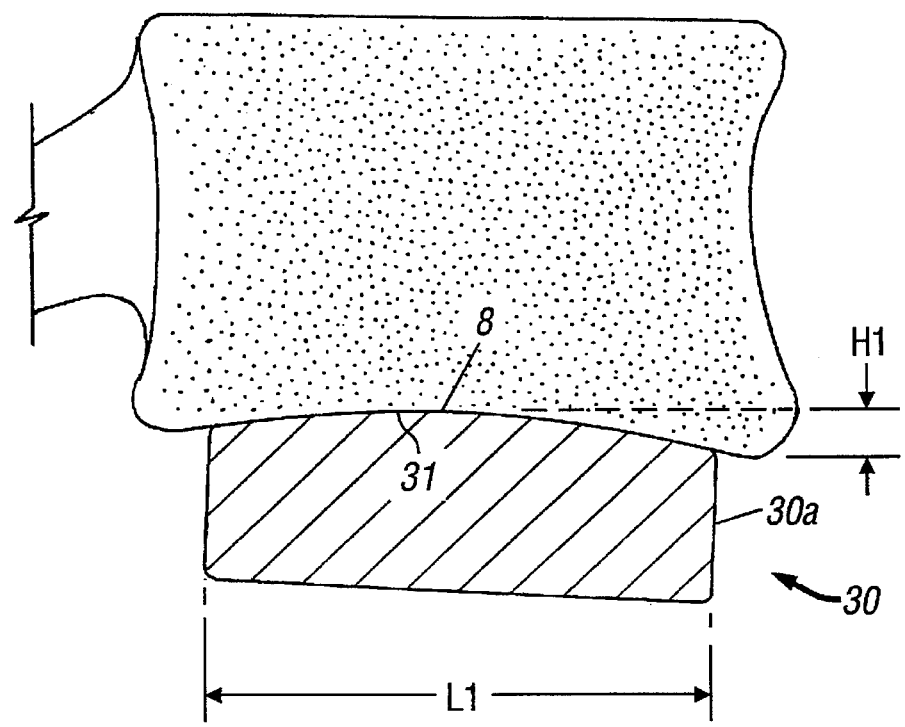
FIG. 14 is a side-sectional view of FIG. 13 taken along lines 14—14 of FIG. 13.

FIGS. 11–14 illustrate the "bowl" contour of an inferior endplate (B). This contour is essentially concave in shape throughout a majority of the endplate surface in both the anterior/posterior dimension (i.e. the Y-axis) and the lateral dimension (i.e. the X-axis). The depth (D2) of the concavity (8) defining the bowl is from about 2 mm to about 5 mm, as shown in FIG. 11A. FIGS. 13–14 illustrate one embodiment of the present invention (30) wherein the fixed shape of the superior surface integral with the body (30a) of the inventive device is a convexity (31). Preferably, the height (H1) of the convexity is approximately the same as the depth (D2) of the concavity (8) of the inferior endplate, in particular from about 2 mm to about 5 mm. As shown in FIGS. 13–14, the convexity (31) of the superior surface of the device fits securely within (i.e. accommodates) the concavity (8) defining the "bowl" contour of the inferior endplate to contact substantially all points along the bowl-shaped portion of the inferior endplate surface.

Figure 15:
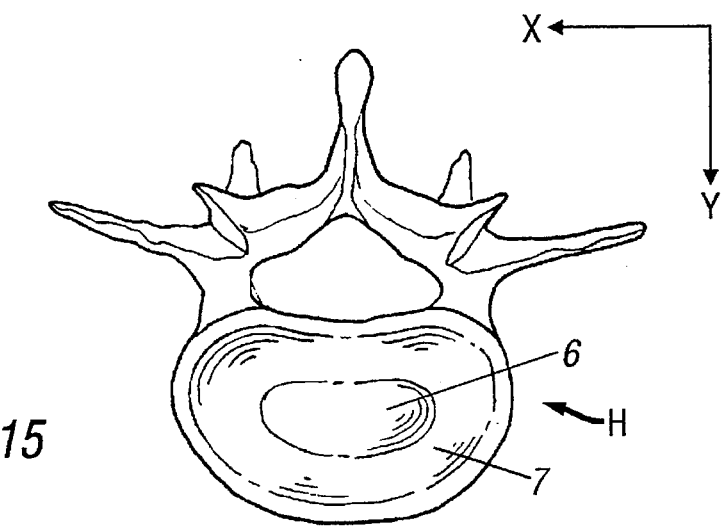
FIG. 15 is a bottom view of an inferior vertebral endplate having a "hump" shape.
Figure 15A:
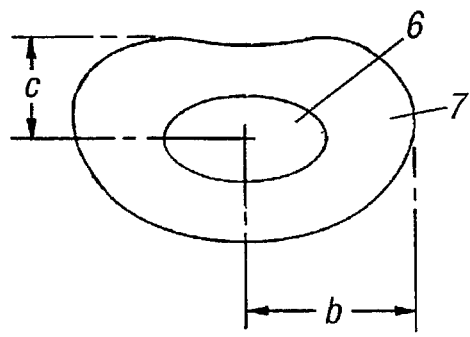
FIG. 15A is a top view of a hump contour of an inferior vertebral endplate.
Figure 16:
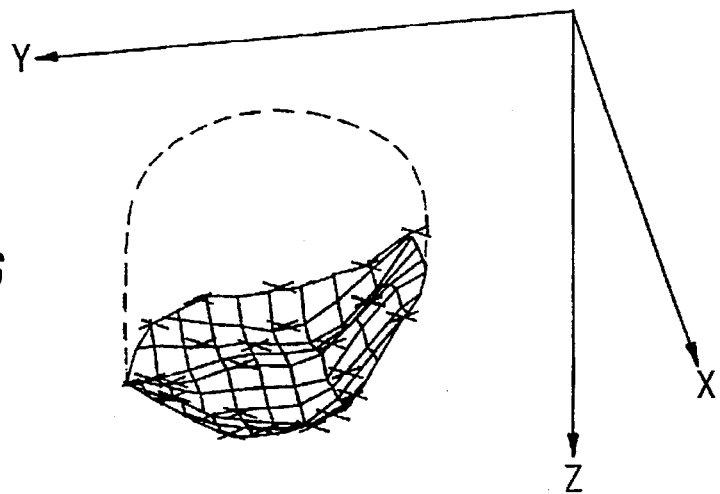
FIG. 16 is a 3-dimensional computer-generated plot of a "hump-shaped" inferior vertebral endplate, the vertical scale of which has been expanded 10×.

FIGS. 15–18 illustrate the "hump" contour of an inferior endplate (H). Here, the surface of the endplate comprises a substantially rounded convexity or hump (6) positioned substantially in the center (b) of the endplate along the lateral dimension, as shown in FIG. 15 and 15A. In the anterior/posterior dimension (c), the hump (6) may be positioned either centrally or up to about 20% of the anterior-posterior dimension closer towards the anterior end. The contour of this endplate generally comprises a circular trough (7) surrounding the hump (6).

Figure 17:
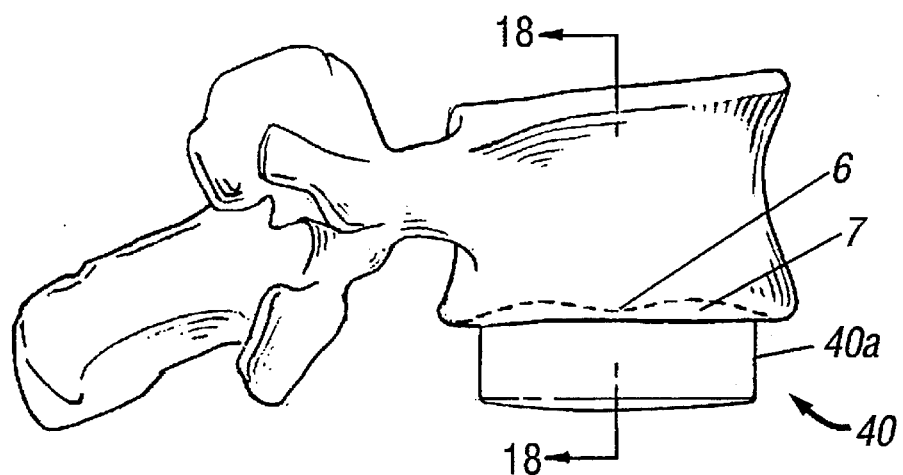
FIG. 17 is a right side elevation view of FIG. 15 further illustrating another embodiment of the inventive device positioned on the surface of the "hump-shaped" inferior vertebral endplate.
Figure 18:
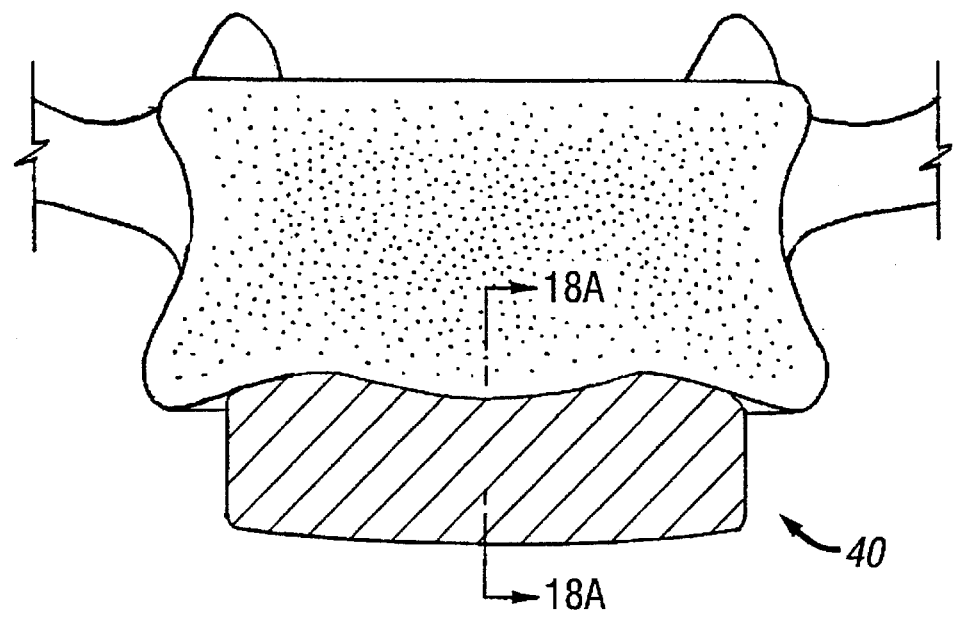
FIG. 18 is a front elevation view taken along lines 18—18 of FIG. 17.
Figure 18A:
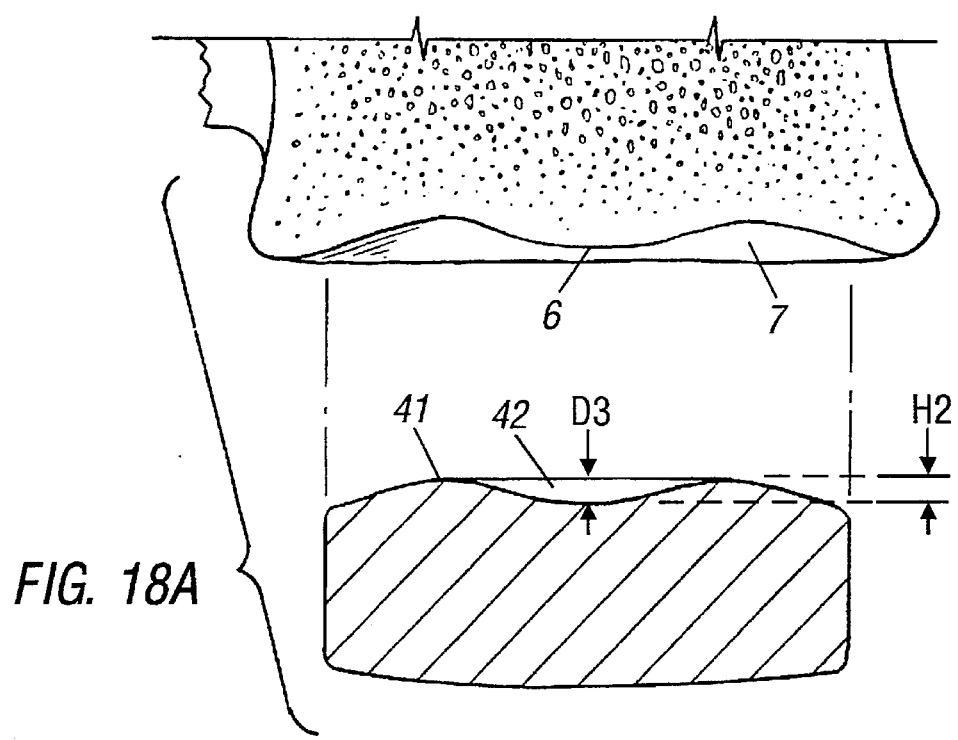
FIG. 18A is an exploded cross-sectional view of the endplate and device taken along lines 18a—18a of FIG. 18.

FIGS. 17–18 illustrate one embodiment (40) of the present invention wherein the fixed shape of the superior surface integral with the body (40a) of the inventive device comprises a concavity (42) positioned centrally in the lateral dimension of the device and a convex ring (41) integral with and surrounding the concavity (42). As shown in FIGS. 17 and 18, the concavity (42) and the convex ring (41) of the superior surface of the device rests securely within (i.e. accommodates) the hump (6) and trough (7), respectively, to contact substantially all points along these contours of the endplate surface. Consequently, the depth (D3) of the concavity (42) is preferably from about 1 mm to about 3 mm, and the height (H2) of the convex ring (41) is preferably from about 2 mm to about 5 mm (i.e. the typical dimensions of the hump and trough contours of the endplate, respectively).

Figure 19:
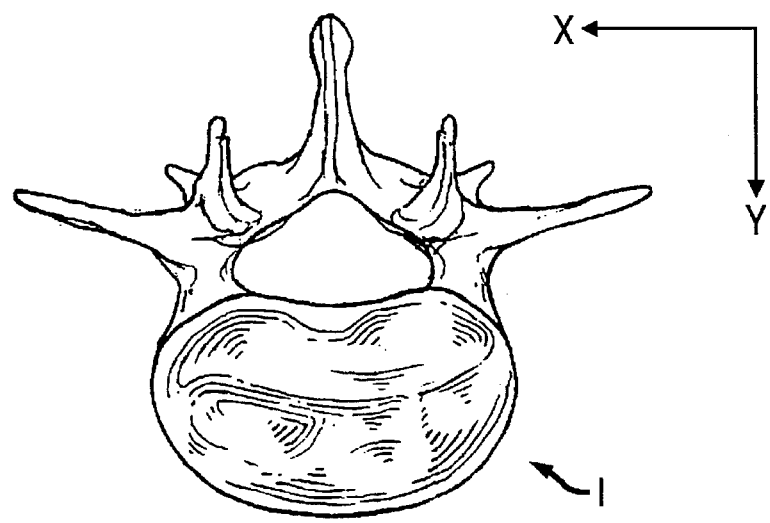
FIG. 19 is a top view of a superior vertebral endplate having an irregularly-shaped contour.
Figure 20:
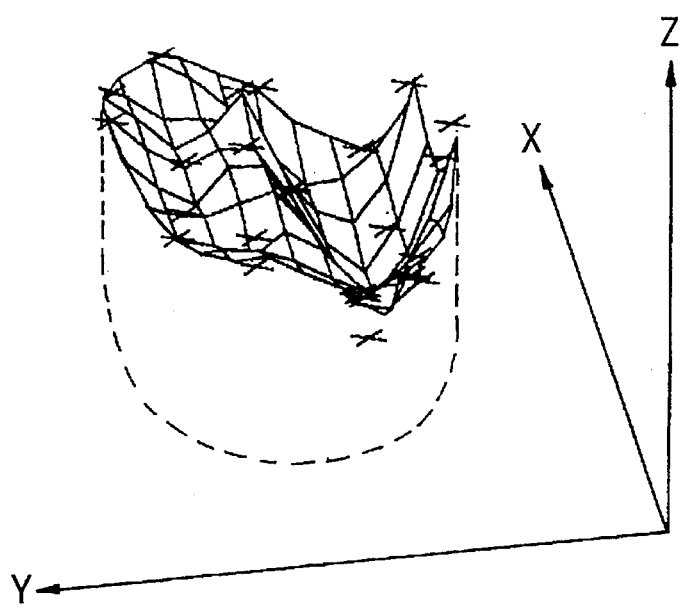
FIG. 20 is a 3-dimensional computer-generated plot of an "irregularly-shaped" superior vertebral endplate, the vertical scale of which has been expanded 10×.

FIGS. 19 and 20 illustrate the "irregular" contour of a superior endplate (I). Unlike the other four morphological groups, the irregularly-shaped superior endplates have few, if any, defined contours which are consistent with other irregularly-shaped endplates. Thus, embodiments of the inventive devices may need to be customized to fit the particular irregularly shaped endplate, or it may be necessary to surgically alter the irregularly shaped surface of the endplate by shaving it down to a relatively flat surface, for example. Alternatively, the inferior surface of the inventive device may comprise relatively flat surfaces to accommodate the irregular contours of the endplate as closely as possible without having to customize the device, or the inferior surface may be formed of an expandable or pliable material which is capable of conforming to the irregular contours of the endplate surface.

The total height or thickness (i.e. along the Z-axis) of the inventive devices may vary greatly depending on the size of intervertebral space remaining. Likewise, the anterior/posterior dimensions as well as the lateral widths of the inventive devices will also vary depending upon the anatomy of the individual patient. The preferred height or thickness (T1) of the devices for use in the thoracic and lumbar spinal region, as shown, for example in FIGS. 5 and 9, is from about 0.5 cm to about 2 cm. In the reconstruction of a single disc space, the preferred thickness is from about 1.5 to about 2 cm. The preferred anterior/posterior length (L1) (i.e. along the Y-axis) is from about 2 cm to about 5 cm, more preferably from about 3 cm to about 5 cm, as shown in FIGS. 5 and 14, for example. Finally, the preferred lateral width (W2) (i.e. along the X-axis) of the device, as shown, for example, in FIG. 13, is from about 3 cm to about 8 cm, more preferably from about 4 cm to about 7 cm.

Figure 21:
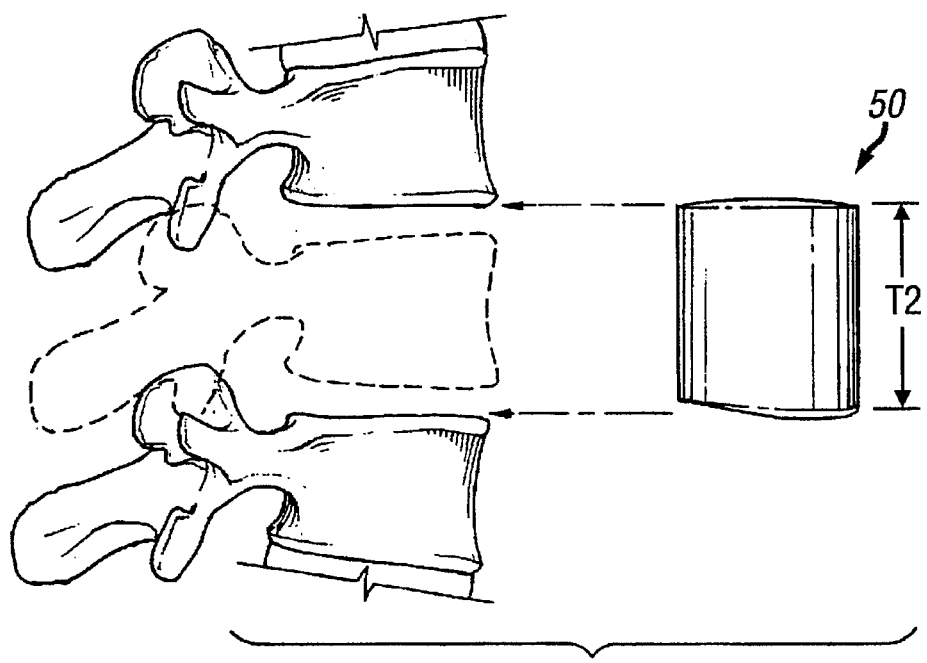
FIG. 21 illustrates an embodiment of the inventive intervertebral device designed to reconstruct a corpectomy.
Figure 22:
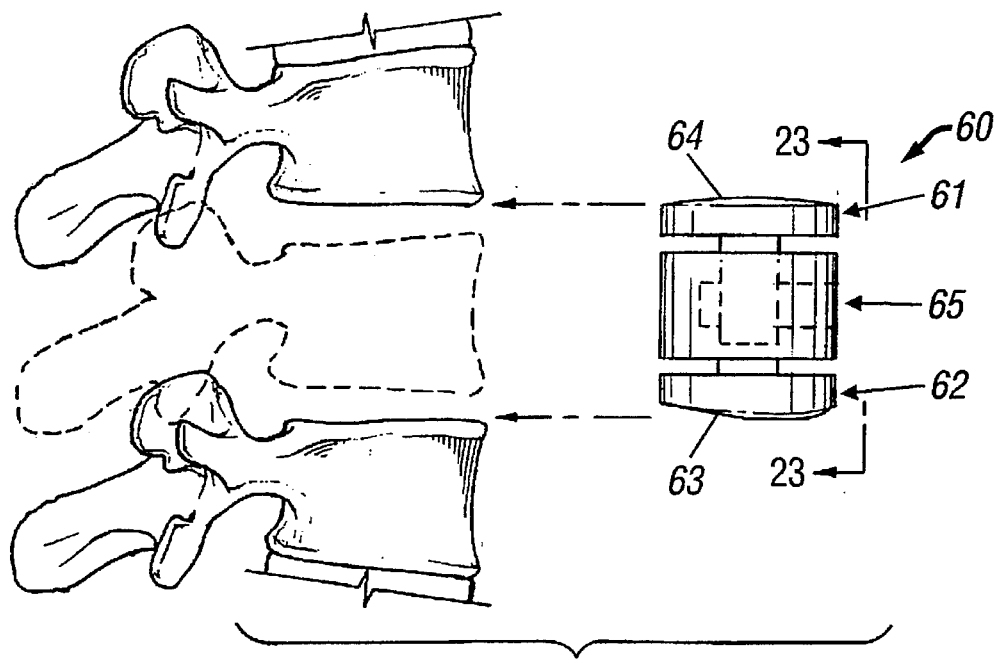
FIG. 22 illustrates a second embodiment of the inventive intervertebral device designed to reconstruct a corpectomy.

The present invention is also directed to intervertebral devices designed to reconstruct the space created by a total corpectomy. A corpectomy, as illustrated in part in FIGS. 21–22, is a surgical procedure wherein an entire vertebral body is removed along with the adjacent superior and inferior intervertebral discs. As shown in FIG. 21, the same inventive devices as described for use in the repair of a space created by the removal of a single disc are employed. However, instead of accommodating the endplates of two adjacent vertebrae (e.g. L-3 and L-4), the inventive device (50) would accommodate two non-contiguous vertebrae (e.g. L-3 and L-5, where L-4 has been removed). Since a larger space is created by a corpectomy, the preferred thickness (T2) or height of this embodiment of the present invention, as illustrated in FIG. 21, is from about 4 cm to about 12 cm.

Figure 23:
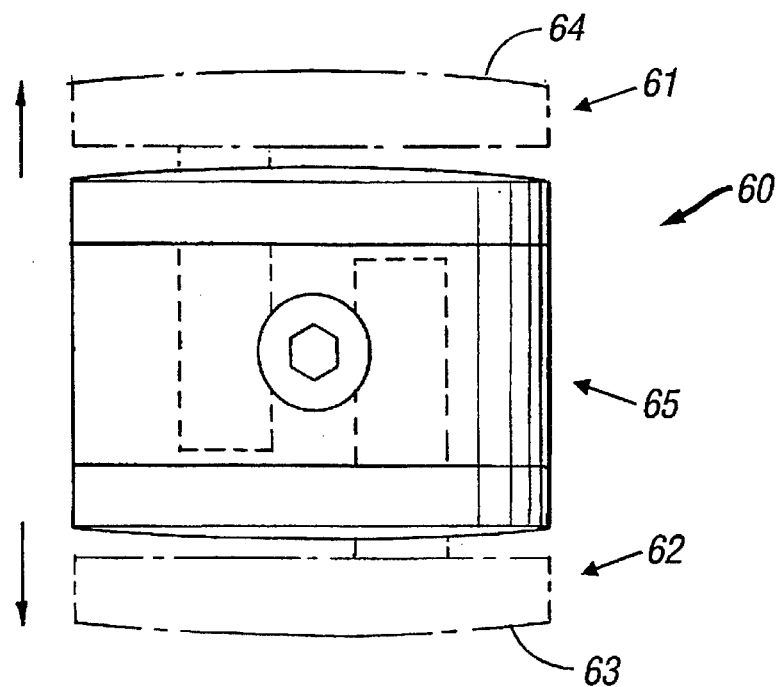
FIG. 23 is a front elevation view of the second embodiment of the inventive intervertebral device taken along lines 23—23 of FIG. 22.

Alternatively, an intervertebral device comprising a rack and pinion ratchet mechanism may also be employed. Referring now to FIGS. 22 and 23, this embodiment (60) comprises a body having a central portion (65), and a top end (61) and a bottom end (62) that are not integral with the central portion (65), but rather are capable of adjusting up or down to accommodate substantially the defined contours of the superior and inferior vertebral endplates. That is, the superior surface (64) of the top end (61) has a fixed shape to accommodate substantially defined contours of an inferior vertebral endplate (e.g. "bowl" and "hump"), and the inferior surface (63) of the bottom end (62) has a fixed shape to accommodate substantially defined contours of a superior vertebral endplate (e.g. "saddle," "ramp," and possibly "irregular").

In addition to the embodiments of the inventive devices described and illustrated herein, the inventive fixed shapes of the superior and inferior surfaces may be applied to the superior and inferior surfaces of other types of intervertebral devices. That is, in certain embodiments, the body of the inventive intervertebral device may be that of other intervertebral devices, grafts, or implants, examples of which include, but are not limited to, expandable disc prostheses, allograft and autograft sections, titanium cages, graphite boxes, spiked prosthetic intervertebral implants, such as AcroMed's AcroFlex Artificial Disc and AMSET's Rezaian Spinal Fixator, and ceramic spacers.

The present invention is also directed to intervertebral devices comprising at least one osteoinductive material. Suitable osteoinductive materials include, but are not limited to, bone extracts and bone growth factors. Examples of bone growth factors include insulin-like bone growth factors (e.g. IGF-I and IGF-II), transforming growth factor $\beta$ (e.g. TGF$\beta_1$ and TGF$\beta_2$), basic fibroblast growth factor (Basic FGF), acidic fibroblast growth factor (acidic FGF), platelet derived growth factor (PDGF), and bone morphogenetic proteins (e.g. BMP-1, BMP-2, BMP-3, BMP-4, BMP-5, BMP-6, and BMP-7). Other terms synonymous with bone growth factors include Somatomedan C, Skeletal Growth Factor, Cartilage Reducing Factor A, Cartilage Reducing Factor B, BMP-2a, BMP-2b, osteogenin, and osteogenic protein-1.

Preferably, the inventive devices comprising at least one osteogenic material have fixed shapes on their respective inferior and superior surfaces for accommodating the defined morphology of the superior and inferior endplates, as discussed herein. However, the inventive devices that incorporate or contain at least one osteoinductive material may have different surface shapes or designs.

The use of such osteoinductive materials, more preferably bone morphogenetic proteins, is advantageous in that these materials function to facilitate bone growth into the intervertebral device for better stabilization and repair of the disc space. The incorporation of an osteoinductive material in the inventive intervertebral devices is particularly preferable when the superior endplate involved has irregularly-shaped contours (I), such that customizing an intervertebral device may be difficult. In such a case, increased bone growth into the device facilitated by the osteoinductive material may compensate for the lack of an optimal fit between the inferior surface of the device and the superior endplate.

Figure 24:
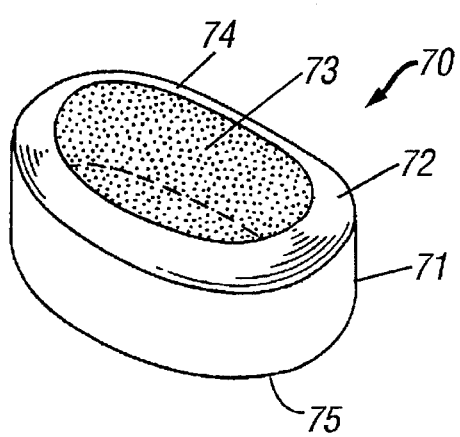
FIG. 24 is a perspective view of a embodiment of the inventive intervertebral device incorporating an osteoinductive material.
Figure 25:
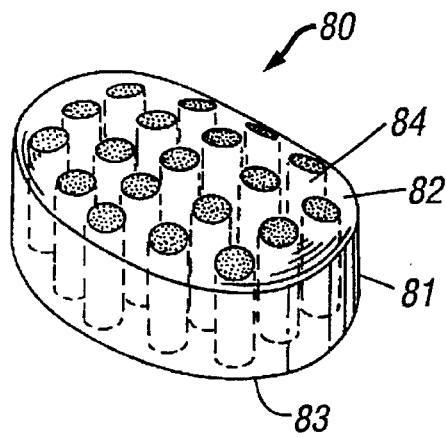
FIG. 25 a perspective view of a second embodiment of the inventive intervertebral device having a plurality of chambers containing an osteoinductive material.
Figure 26:
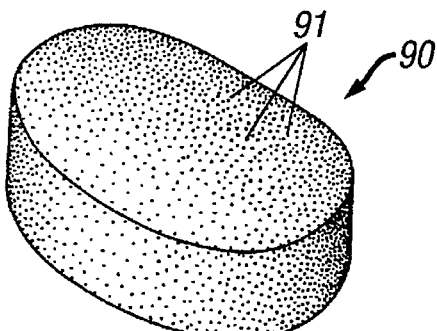
FIG. 26 a perspective view of a third embodiment of the inventive intervertebral device having a plurality of pores containing an osteoinductive material.

There are various means by which an osteoinductive material may be incorporated into the inventive devices. Typically, the osteoinductive material is incorporated into some type of matrix, such as collagen gel, for example, prior to being formed or incorporated into the inventive intervertebral device. FIGS. 24–26 illustrate three preferable embodiments of the present invention which incorporate at least one osteoinductive material; however, it is contemplated that one of ordinary skill in this art who has the benefit of this invention's teachings and suggestions may be capable of constructing variations of these embodiments to achieve the same results.

Referring now to FIG. 24, this embodiment of the inventive device (70) comprises a) a body (71) having a reservoir (73) containing at least one osteoinductive material and an outer ring (72) that is integral with and surrounds the reservoir; b) a superior surface (74) integral with the body; and c) an inferior surface (75) integral with the body. Preferably, the osteoinductive material contained in the reservoir is incorporated in some solid or gelatinous matrix such as hydroxyapatite or collagen, for example. The outer ring (72) may be formed of any material normally used in the manufacture of orthopedic implants, including, but not limited to, metals, metal alloys, and ceramics. More preferable materials include titanium and titanium alloys.

FIG. 25 illustrates a second embodiment of the present invention (80) for incorporating an osteoinductive material. In this embodiment, the body (81) of the inventive device comprises at least one chamber (84) communicating between the superior surface (82) and inferior surface (83) of the device. Contained within each chamber is at least one osteoinductive material which is preferably incorporated in some solid or gelatinous matrix, such as collagen gel, for example.

FIG. 26 illustrates a third embodiment of the present invention (90), wherein the osteoinductive material is contained within a plurality of pores (91) present throughout the device. As with the first two embodiments, the osteoinductive material is preferably incorporated in some solid or gelatinous matrix, such as hydroxyapatite or calcium phosphate ceramic, for example.

Figure 27:
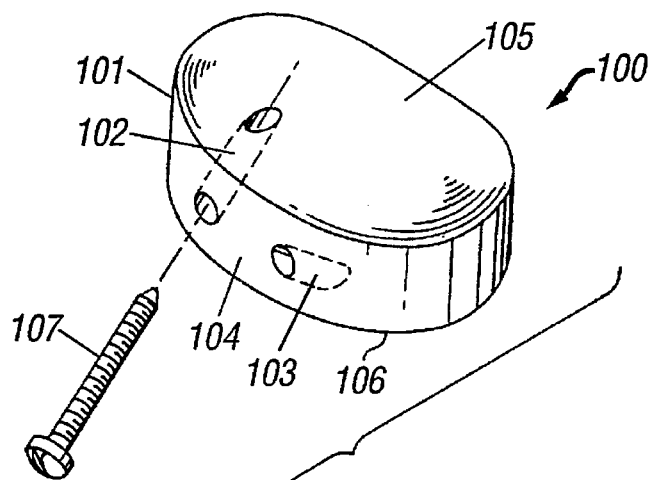
FIG. 27 illustrates an alternate embodiment of the inventive device comprising an additional means for securing the device to the adjacent vertebral endplates.

Because the types and dimensions of the inventive fixed shapes are designed to accommodate substantially the defined contours of specific vertebral endplate surfaces, the surgeon is better able to fit the inventive device securely between the superior and inferior vertebral endplates. FIG. 27, however, illustrates an alternate embodiment of the present invention (100) and comprises a means for further securing the device to the vertebrae. In this embodiment, the device further comprises at least one angled bore (102) communicating between the anterior wall (104) of the body (101) and the superior surface (105) of the device. Likewise, the device may comprise at least one angled bore (103) communicating between the anterior wall (104) of the body (101) and the inferior surface (106) of the device. Once the inventive device is inserted in the disc space, the device may be further secured to the superior and inferior endplates by means of a screw (107), for example, which is first inserted into the angled bores, and then into the respective superior and inferior endplates. Other suitable fasteners include, but are not limited to, pins, bolts, and wires.

While the superior and inferior surfaces of the devices shown in FIGS. 24–27, as well as obvious modifications thereof, may be of any desired shape for reconstruction of intervertebral disc spaces throughout the spine, the most preferred embodiments comprise superior and inferior surfaces having the inventive fixed shapes discussed herein for accommodating substantially the defined contours of superior (e.g. "ramp" and "saddle") and inferior (e.g. "bowl" and "hump") endplates, more particularly those endplates in the thoracic and lumbar spinal regions.

Determination of Morphology of Vertebral Surfaces

The present invention is also directed to a method for quantitatively determining the specific morphology of bone surfaces, in particular vertebral surfaces throughout the spine, and more particularly the surfaces of vertebral endplates.

Figure 28:
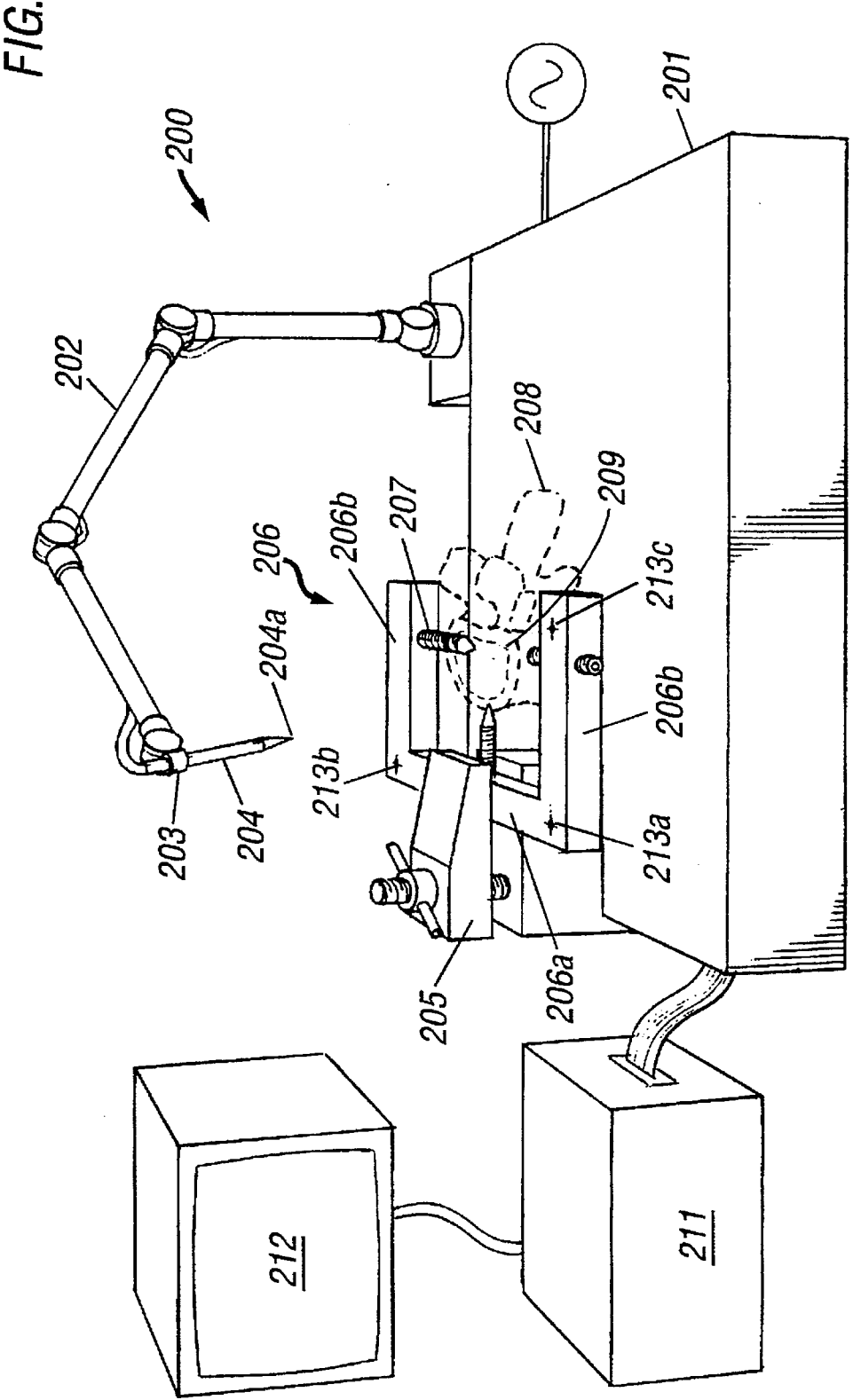
FIG. 28 is a schematic view of the inventive digitization method set-up for quantitatively determining the morphology of bone surfaces (a vertebral endplate is illustrated).
Figure 29:
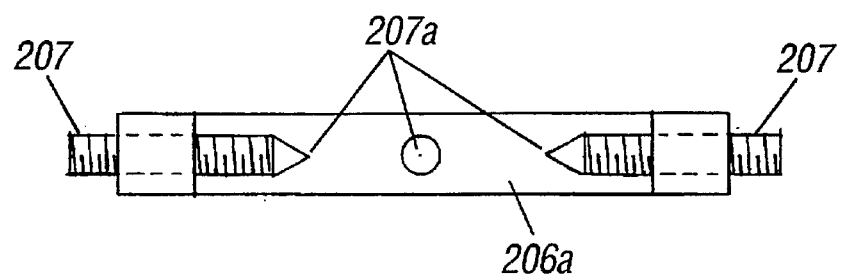
FIG. 29 is a front elevation view of the "C"-shaped clamp used for quantitatively determining the morphology of bone surfaces.
Figure 30:
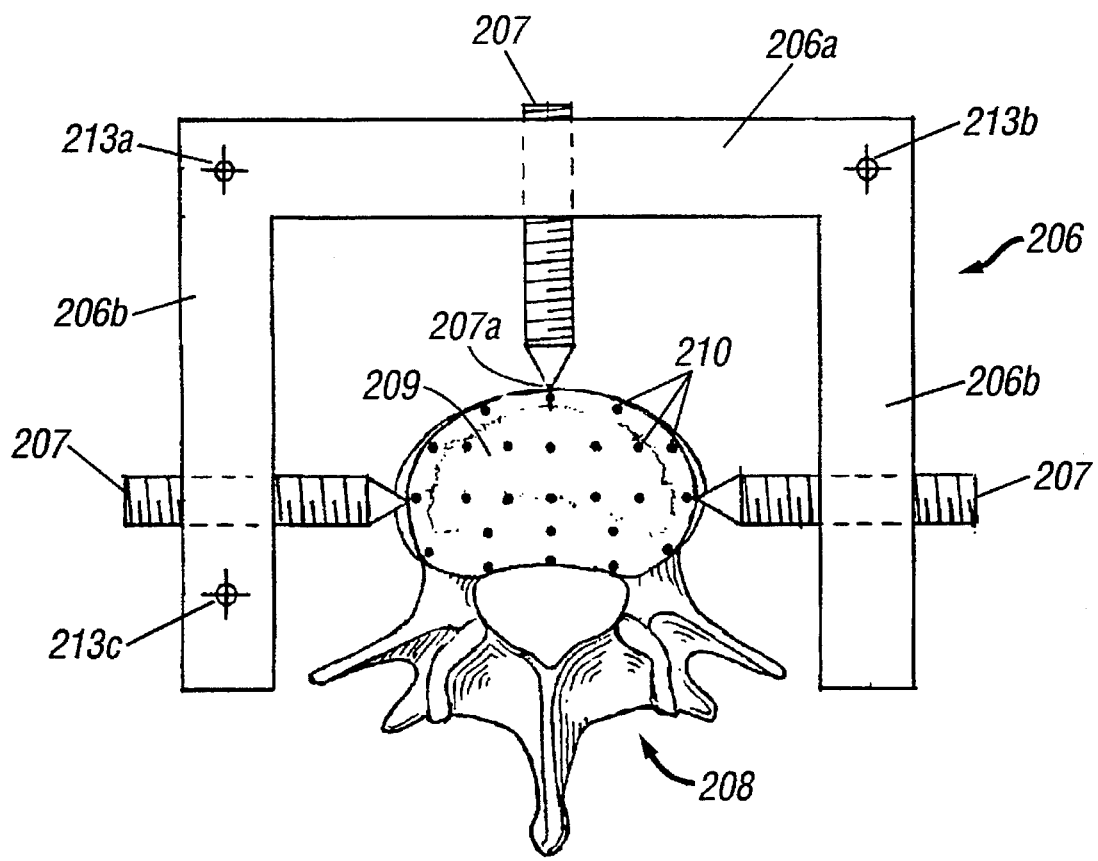
FIG. 30 is a top plan view "C"-shaped clamp engaging a vertebral endplate for digitization. Also viewed are the points marked on the vertebral endplate for digitization.

Referring now to FIGS. 28–30, the inventive method comprises the use of a digitization process (200) for generating a three-dimensional plot of the vertebral surface. In the case of vertebral endplates, a plurality of points (210) are located on the surface of the endplate (209). These points represent landmarks such as high and low points, corners, and the edges of the cortical rim. Preferably for endplates in the lower thoracic and lumbar regions (i.e. T11–L5), a total of from about 20 to about 30 points should be located, preferably as shown in FIG. 30, for example. Similarly, the total number of points that should be identified on the surfaces of cervical and upper thoracic vertebra (i.e. T1–T10) should preferable be from about 20 to about 30 points.

Once the points are selected and marked on the vertebral surface, a clamp, preferably a 3-point "C"-type clamp (206), is attached to the vertebral body (208) by a securing means (207) preferably having piercing tips (207a) for securely holding the vertebral body in place during the digitization process. Prior to digitization, the clamp may be secured to the digitizer by means of a vise (205), for example. The C-clamp, which is preferably rigid in form, has a posterior member (206a) and two arms (206b), each arm being integral with and perpendicular to each end of the posterior member, as shown FIGS. 28 and 30. Thus, the posterior member and the two arms of the clamp form a C-shape which define an inner void (205) for placement of the vertebra (208), or any other bone surface for which digitization is to be performed.

The inventive C-clamp (206) contains small depressions (213) which serve to define a coordinate system (i.e. the origin (213a), X-axis (213b), and Y-axis (213c)) for the digitization of the three-dimensional coordinates of the points marked on the vertebra. Thus, the three depressions are digitized using a three-dimensional digitizer (201) at the start of the measurement process to define the origin, X-axis, and the XY plane. Whenever the vertebral body (208) is moved during the digitization process (for example, to access points on the inferior side of the vertebral surface), these three reference points are redigitized.

Once the three-dimensional coordinate system has been established, the selected points on the vertebral surface are digitized with the three-dimensional digitizer (201). Preferably the digitizer comprises a sharp stylus (204) attached to a base point (203) by a multiply-jointed arm (202). The tip (204a) of the stylus is placed on each point (210) to be digitized, and upon activation of the digitizer, the three coordinates of the point are recorded in a computer file contained in a processor (211). The digitizer may also include a monitor (212) for displaying the values of the coordinates measured.

In measuring the morphology of vertebral endplates, particularly in the lower thoracic and lumbar spinal regions, each vertebra has three data sets recorded: the superior endplate, the inferior endplate, and the tips of the transverse process and spinous processes. These are combined in order to transform the coordinates of the endplate points to a coordinate system based on the anatomic planes.

The data from each endplate are fit to a surface using the following equation for the Hardy multiquadric:

$$M(x,y) = \sum_{i=1}^{N} \alpha_i \, [(x-x_i)^2 + (y-y_i)^2 + R^2]^{0.5}$$

where $\alpha_i$ satisfies the N×N linear system of equations generated by including N data points in the above equation, and $R^2$ is a parameter sensitive to the average distance between the data points. This algorithm has been described in several scientific papers, and a program is made available by T. Foley [Foley, T. A., *Comput. Math Applic.*, 13(8): 711–740 (1987)]. The original algorithm was described by R. L. Hardy in *J. Geophys. Res.*, 76:1905–1915 (1971) and was developed for reducing topographical data from geophysical surveys to a concise mathematical form.

The following examples do not limit the scope of the invention but are intended to illustrate various aspects of the invention.

EXAMPLE 1

Ten dried thoracolumbar spines, T11–L5, were gathered. A total of sixty-seven vertebrae were available: eight columns containing T11–L5, one column contain T12–L5, and one column containing L1–L5 for a total of 134 endplates. Each vertebral body was marked with 54 points: 25 points on each endplate, one point on the tip of each transverse process, and two points on the posterior-most aspect of the spinous process. A 3-point "C"-type clamp with piercing tips was attached to each vertebra to begin the measurement process. Three points, marked with small depressions in the body of the clamp, served to define a coordinate system (i.e. the origin, X-axis, and XY plane) for the digitization of the 3-dimensional coordinates of the points marked on the vertebrae. Whenever the vertebra was moved during the digitization process, these three reference points were redigitized to ensure that all points were acquired relative to the same coordinate system.

The digitizer used was an electromagnetic device (Metrecom System, Faro Medical Technologies, Lake Mary, Fla.) having a resolution of 0.1 mm. The digitizer comprised a sharp stylus attached to a base point by a multiply-jointed arm. The tip of the stylus was placed on each point to be digitized. The depression of a button recorded the coordinates (i.e. three numerical values) of the tip in a computer file. Measurements were in tenths of millimeters. Each vertebra had three data sets recorded—the superior endplate, the inferior endplate, and the tips of the transverse and spinous processes. These were combined in order to transform the coordinates of the endplate points to a coordinate system based on the anatomic planes. The endplate data point coordinates were transformed from the coordinate system based on the C-clamp to one based on the spinous and transverse processes. This placed the endplate data in a more natural orientation with respect to the anatomical coordinate planes. In addition, this step had the benefit of placing the superior endplate and the inferior endplate data from each vertebra in their natural orientation.

The 25 points on each endplate were chosen to represent characteristic landmarks such as high and low points, corners, and the edges of the cortical rim. These points were used to calculate a best-fit surface using the Hardy Multiquadric algorithm, afterwhich three-dimensional plots of these surfaces were generated to classify the endplate morphologies.

Each plot was examined for the presence or absence of each of the following features: irregular posterior border, extreme irregularity, central hump, anterior ramp, and bowl. These features, when tabulated for all endplates, were classified into five shape type: "ramp," "saddle," "irregular," "bowl," and "hump." Finally, the twenty-five data points on the endplates from each group were then combined to generate an average surface for each shape type.

EXAMPLE 2

Of the sixty-seven superior vertebral endplates digitized according to the method described in Example 1, eighteen endplates (27%) were found to have a "saddle" contour, thirty-one endplates (46%) were found to have a "ramp" contour, and eighteen endplates (27%) were found to have an "irregular" contour. Three-dimensional plots were generated as described in Example 1, including the plots shown in FIG. 4 for the "saddle" shaped endplate, FIG. 8 for the "ramp" shape endplate, and FIG. 20 for the "irregular" shape. The Z-axis for each plot represented the plane defined by the bottom or inferior end (at the origin) and the top or superior end (at the arrow) of the endplate. The X-axis represented the plane defined by the left side (at the origin) and the right side (at the arrow) of the endplate. The Y-axis represented the front or anterior end (at the origin) and the back or posterior end (at the arrow) of the endplate. The vertical scales of the three-dimensional plots were magnified approximately 10× to enhance the individual contours.

EXAMPLE 3

Of the sixty-seven inferior vertebral endplates digitized according to the method described in Example 1, forty-seven (70%) endplates were found to have a "bowl" contour and twenty endplates (30%) endplates were found to have a "hump" contour. Three-dimensional plots were generated as described in Example 1, including the plots shown in FIG. 12 for the "bowl" shaped endplate and FIG. 16 for the "hump" shape endplate. The Z-axis for each plot represented the planes defined by the bottom or inferior end (at the origin) and the top or superior end (at the arrow) of the endplate. The X-axis represented the plane defined by the left side (at the origin) and the right side (at the arrow) of the endplate. The Y-axis represented the plane defined by the front or anterior end (at the origin) and the back or posterior end (at the arrow) of the endplate. The vertical scales of the three-dimensional plots were magnified approximately 10× to enhance the individual contours.

The foregoing disclosure and description of the invention are illustrative and explanatory thereof, and various changes in the size, shape, and materials, as well as in the details of the illustrated construction may be made without departing from the spirit of the invention.

We claim:

1. A prosthetic intervertebral device comprising:
   (a) a body for insertion into an intervertebral disc space;
   (b) a superior surface integral with said body and having an anterior end, a posterior end, a left side, and a right side, and wherein said superior surface has a fixed shape which is configured to match the contours of an inferior vertebral endplate; and
   (c) an inferior surface integral with said body and having an anterior end, a posterior end, a left side, and a right side, and wherein said inferior surface has a fixed shape which is configured to match the contours of a superior vertebral endplate.

2. The device of claim 1, wherein said fixed shape of said inferior surface comprises
   a) a first and second convexity, said first convexity positioned on said right side of said inferior surface and said second convexity positioned on said left side of said inferior surface; and
   (b) a longitudinal portion positioned centrally between said first and second convexities and along the posterior and anterior ends of said inferior surface for accommodating an elevated ridge of said superior vertebral endplate, said longitudinal portion further including, in a series, a concavity positioned anteriorly along said longitudinal portion, a third convexity positioned adjacent to said concavity, and a ramp positioned adjacent to said third convexity and posteriorly along said longitudinal portion.

3. The device of claim 1 wherein said fixed shape of said inferior surface comprises, in a series, a ramp positioned on said posterior end of said surface and a lower plane extending from said ramp toward said anterior end of said surface.

4. The device of claim 1, wherein said fixed shape of said superior surface is a convexity for accommodating a bowl-shaped inferior vertebral endplate.

5. The device of claim 1, wherein said fixed shape of said superior surface comprises a concavity positioned centrally between the left end and the right end of said superior surface and a convex ring integral with and surrounding said concavity.

6. The device of claim 2, wherein said fixed shape of said superior surface is a convexity for accommodating a bowl-shaped inferior vertebral endplate.

7. The device of claim 6, wherein said body is formed of a material comprising at least one bone growth factor.

8. The device of claim 6, wherein said superior surface convexity is from about 2 mm to about 5 mm in height, said inferior surface first and second convexities are from about 2 mm to about 5 mm in height, and said inferior surface longitudinal portion is from about 1 mm to about 4 mm in depth.

9. The device of claim 2, wherein said fixed shape of said superior surface comprises a concavity positioned centrally between the left end and the right end of said superior surface and a convex ring integral with and surrounding said superior surface concavity.

10. The device of claim 9 wherein said body is formed of a material comprising at least one bone growth factor.

11. The device of claim 9 wherein said superior surface concavity is from about 1 mm to about 3 mm in depth, said superior surface convex ring is from about 2 mm to about 5 mm in height, said inferior surface first and second convexities are from about 2 mm to about 5 mm in height, and said inferior surface longitudinal portion is from about 1 mm to about 4 mm in depth.

12. The device of claim 3, wherein said fixed shape of said superior surface is a convexity for accommodating a bowl-shaped inferior vertebral endplate.

13. The device of claim 12, wherein said body is formed of a material comprising at least one bone growth factor.

14. The device of claim 12, wherein said superior surface convexity is from about 2 mm to about 5 mm in height, said inferior surface ramp is from about 10 mm to about 30 mm in length, and said inferior surface lower plane is from about 10 mm to about 40 mm in length.

15. The device of claim 3, wherein said fixed shape of said superior surface comprises a concavity positioned centrally between the left and right ends of said superior surface and a convex ring integral with and surrounding said superior surface concavity.

16. The device of claim 15 wherein said body is formed of a material comprising at least one bone growth factor.

17. The device of claim 15 wherein said superior surface concavity is from about 1 mm to about 3 mm in depth, said superior surface convex ring is from about 2 mm to about 5 mm in height, said inferior surface ramp is from about 10 mm to about 30 mm in length, and said inferior surface lower plane is from about 10 mm to about 40 mm in length.

18. The device of claim 1, wherein said body further comprises at least one chamber communicating between said superior surface and said inferior surface, said at least one chamber containing at least one osteoinductive material.

19. The device of claim 18, wherein said at least one osteoinductive material is a bone morphogenetic protein.

20. The device of claim 1 wherein said body further comprises a plurality of pores containing at least one osteoinductive material.

21. The device of claim 20 wherein said at least one osteoinductive material is a bone morphogenetic protein.

22. A prosthetic intervertebral device for insertion into a vertebral disc space comprising:
   (a) a body, said body further comprising a reservoir containing at least one osteoinductive material, and an outer ring integral with and surrounding said reservoir;
   (b) a superior surface integral with said body, wherein said superior surface has a fixed shape which is configured to match the contours of an inferior vertebral endplate; and
   (c) an inferior surface integral with said body, wherein said inferior surface has a fixed shape which is configured to match the contours of a superior vertebral endplate.

23. The device of claim 22 wherein said fixed shape of said inferior surface comprises
   a) a first and second convexity, said first convexity positioned on said right side of said inferior surface and said second convexity positioned on said left side of said inferior surface; and
   (b) a longitudinal portion positioned centrally between said first and second convexities and along the posterior and anterior ends of said inferior surface for accommodating an elevated ridge of said superior vertebral endplate, said longitudinal portion further including, in a series, a concavity positioned anteriorly along said longitudinal portion, a third convexity positioned adjacent to said concavity, and a ramp positioned adjacent to said third convexity and posteriorly along said longitudinal portion;

and wherein said fixed shape of said superior surface of said device comprises a fourth convexity for accommodating a bowl-shaped inferior vertebral endplate.

24. The device of claim 23, wherein said at least one osteoinductive material is a bone growth factor.

25. The device of claim 22 wherein said fixed shape of said inferior surface comprises:

a) a first and second convexity, said first convexity positioned on said right side of said inferior surface and said second convexity positioned on said left side of said inferior surface; and (b) a longitudinal portion positioned centrally between said first and second convexities and along the posterior and anterior ends of said inferior surface for accommodating an elevated ridge of said superior vertebral endplate, said longitudinal portion further including, in a series, a first concavity positioned anteriorly along said longitudinal portion, a third convexity positioned adjacent to said first concavity, and a ramp positioned adjacent to said third convexity and posteriorly along said longitudinal portion;

and wherein said fixed shape of said superior surface comprises a second concavity positioned centrally between the left end and the right end of said superior surface and a convex ring integral with and surrounding said superior surface concavity.

26. The device of claim 25, wherein said at least one osteoinductive material is a bone growth factor.

27. The device of claim 22, wherein said fixed shape of said inferior surface comprises, in a series, a ramp positioned on said posterior end of said inferior surface and a lower plane extending from said ramp toward said anterior end of said inferior surface;

and wherein said fixed shape of said superior surface is a convexity for accommodating a bowl-shaped inferior vertebral endplate.

28. The device of claim 27, wherein said at least one osteoinductive material is a bone growth factor.

29. The device of claim 22 wherein said fixed shape of said inferior surface comprises, in a series, a ramp positioned on said posterior end of said inferior surface and a lower plane extending from said ramp toward said anterior end of said inferior surface;

and wherein said fixed shape of said superior surface comprises a concavity positioned centrally between the left end and the right end of said superior surface and a convex ring integral with and surrounding said superior surface concavity.

30. The device of claim 29, wherein said at least one osteoinductive material is a bone growth factor.

31. A prosthetic intervertebral device comprising:

(a) a body for insertion into an intervertebral disc space;

(b) a superior surface integral with said body for contacting an inferior vertebral endplate; and (c) an inferior surface integral with said body and having an anterior end, a posterior end, a left side, and a right side, and wherein said inferior surface has a fixed shape which is configured to match the contours of a superior vertebral endplate.

32. The device of claim 31, wherein said fixed shape of said inferior surface comprises a) a first and second convexity, said first convexity positioned on said right side of said inferior surface and said second convexity positioned on said left side of said inferior surface; and (b) a longitudinal portion positioned centrally between said first and second convexities and along the posterior and anterior ends of said inferior surface for accommodating an elevated ridge of said superior vertebral endplate, said longitudinal portion further including, in a series, a concavity positioned anteriorly along said longitudinal portion, a third convexity positioned adjacent to said concavity, and a ramp positioned adjacent to said third convexity and posteriorly along said longitudinal portion.

33. The device of claim 31, wherein said fixed shape of said inferior surface comprises, in a series, a ramp positioned on said posterior end of said surface and a lower plane extending from said ramp toward said anterior end of said surface.

34. A prosthetic intervertebral device comprising:

(a) a body for insertion into an intervertebral disc space;

(b) a superior surface integral with said body and having an anterior end, a posterior end, a left side, and a right side, and wherein said superior surface has a fixed shape which is configured to match the contours of an inferior vertebral endplate; and (c) an inferior surface integral with said body for contacting a superior vertebral endplate.

35. The device of 34, wherein said fixed shape of said superior surface is a convexity for accommodating a bowl-shaped inferior vertebral endplate.

36. The device of claim 34, wherein said fixed shape of said superior surface comprises a concavity positioned centrally between the left end and the right end of said superior surface and a convex ring integral with and surrounding said concavity.

* * * * *

UNITED STATES PATENT AND TRADEMARK OFFICE
CERTIFICATE OF CORRECTION

PATENT NO. : 5,514,180
DATED : May 7, 1996
INVENTOR(S) : Michael H. Heggeness and Brian J. Doherty It is certified that error appears in the above-indentified patent and that said Letters Patent is hereby corrected as shown below:

In column 8, line 28, delete "(L1)" and insert -- (L2) --

In column 9, lines 23 and 29, delete "18" and insert -- 18A --

In column 12, line 54, delete "(205)"

In column 12, line 58, delete "(213)" and insert -- (213a, 213b, and 213c) --

Signed and Sealed this

Third Day of December, 1996

Attest:

BRUCE LEHMAN

Attesting Officer   Commissioner of Patents and Trademarks